United States Patent [19]

Wright, Jr. et al.

[11] Patent Number: 5,153,118
[45] Date of Patent: Oct. 6, 1992

[54] MONOCLONAL ANTIBODIES HAVING BINDING SPECIFICITY TO HUMAN PROSTATE TUMOR-ASSOCIATED ANTIGENS AND METHODS FOR EMPLOYING THE SAME

[75] Inventors: George L. Wright, Jr., Virginia Beach, Va.; James J. Starling, Carmel, Ind.

[73] Assignee: Eastern Virginia Medical Authority, Norfolk, Va.

[21] Appl. No.: 262,123

[22] Filed: Oct. 25, 1988

Related U.S. Application Data

[63] Continuation of Ser. No. 941,911, Dec. 15, 1986, abandoned, which is a continuation-in-part of Ser. No. 809,719, Dec. 17, 1985, abandoned.

[51] Int. Cl.[5] .................. A61K 49/02; C07K 15/28; G01N 33/574; G01N 33/577
[52] U.S. Cl. .................. 435/7.23; 424/1.1; 424/9; 424/85.8; 435/7.9; 435/172.2; 435/240.27; 435/948; 436/548; 436/813; 530/809; 530/388.8; 530/391.3; 530/861; 935/107; 935/110
[58] Field of Search .............. 424/1.1, 9, 85.8, 85.91; 435/7, 172.2, 240.27, 948, 7.23, 7.9; 436/548, 813; 530/387, 391, 809; 935/107, 110

[56] References Cited

U.S. PATENT DOCUMENTS

| | | | |
|---|---|---|---|
| 4,446,122 | 5/1984 | Chu et al. | 436/548 |
| 4,690,890 | 9/1987 | Loor et al. | 435/948 |
| 4,970,299 | 11/1990 | Bazinet et al. | 530/387 |

OTHER PUBLICATIONS

G. B. Lipford et al, *Cancer Research*, *51*, 2296–2301, 1991.
G. L. Wright Jr. et al, *Int. Jour. Cancer*, *47*, 717–725, 1991.
R. H. Raynor et al, *The Prostate*, *9*, 21–31, 1986.
T. M. Chu "Monoclonal Antibodies to Human Prostate Cancer-Related Antigens", in S. Sell et al (Eds.) *Monoclonal Antibodies in Cancer*, Humana Press, 1985, pp. 309–324.
A. M. Carroll et al, *Clin. Immunol. Immunopathol.*, *33*, 268–281, 1984.
A. E. Frankel et al, *Proc. Natl. Acad. Sci. USA*, *79*, 903–407, 1982.
J. Lindgren et al, *Hybridoma*, *4*, 37–45, 1985.
D. H. Lowe et al, *Journ. Urology*, *132*, 780–785, 1984.
R. H. Raynor et al, *Journ. Natl. Cancer Inst.*, *73*, 617–625, 1984.
J. J. Starling et al, *Cancer Res.*, *42*, 3084–3089, 1982.
S. M. Clarke et al, *The Prostate*, *3*, 203–214, 1982.
J. J. Starling et al, *Cancer Res.*, *45*, 804–808, 1985.
J. L. Ware et al, *Cancer Res. 42*, 1215–1222, 1982.
K. S. Webe et al, *Cancer Immunol. Immunother.*, *17*, 7–17, 1984.
G. L. Wright, Jr. et al, *Cancer Res.*, *43*, 5509–5516, 1983.

*Primary Examiner*—David Saunders
*Attorney, Agent, or Firm*—Sughrue, Mion, Zinn, Macpeak & Seas

[57] ABSTRACT

Monoclonal antibodies having binding specificity to human prostate tumor-associated antigens but not to prostate-specific antigen (PSA) or prostatic acid phosphatase (PAP); and methods of diagnosis and treatment employing the same.

12 Claims, 2 Drawing Sheets

MONOCLONAL ANTIBODIES HAVING BINDING SPECIFICITY TO HUMAN PROSTATE TUMOR-ASSOCIATED ANTIGENS AND METHODS FOR EMPLOYING THE SAME

CROSS-REFERENCE TO RELATED APPLICATIONS

This is a continuation of application Ser. No. 06/941,911, filed Dec. 15, 1986, abandoned, which is a CIP of application Ser. No. 809,719 filed Dec. 17, 1985, abandoned.

FIELD OF THE INVENTION

The present invention relates to monoclonal antibodies having binding specificity to human prostate tumor-associated antigens but not to prostate-specific antigen (PSA) or prostatic acid phosphatase (PAP); and methods of diagnosis and treatment employing the same.

BACKGROUND OF THE INVENTION

Various monoclonal antibodies have been developed over the years in an attempt to find substances which have binding specificity to tumor-associated antigens It has been hoped that these monoclonal antibodies would be useful in the diagnosis and treatment of tumors.

Monoclonal antibodies are produced by cell lines known as hybridomas. Hybridomas can be created using tumor tissue such that the monoclonal antibodies produced therefrom have binding affinity to antigens associated with the tumor tissue. Most monoclonal antibodies are disadvantageous in that they have either (1) an extreme binding specificity, i.e., they are not capable of binding to many tumor types other than those which are very closely related to the tumor from which they were developed or (2) an extreme lack of binding specificity. i.e. they bind to almost all types of cells whether malignant or non-malignant. As a result, these monoclonal antibodies are generally not clinically useful because due to (1) their extreme binding specificity, a unique monoclonal antibody needs to be developed for each tumor to be diagnosed or treated, or (2) their extreme lack of binding specificity, the monoclonal antibody is incapable of differentiating between malignant and non-malignant cells.

In spite of the concerns which have arisen regarding the usefulness of monoclonal antibodies in diagnostic and therapeutic methods, it is still believed that monoclonal antibodies can be developed which are organ specific, i.e., capable of binding to antigens associated with only a particular organ, but which, given their organ-specificity, are capable of binding to an antigen that is associated with many different types of tumors arising in the particular organ.

Prostate carcinoma is one of the most prevalent malignancies among men in the United States. It is postulated that the disease is often present but undetected in the male population. Moreover, it has been noted that prostate carcinoma often exhibits a long latency period. Further prostate carcinoma is known for its high metastatic potential. For these reasons, it has been desired to develop a substance or substances useful for diagnosing, in vivo or in vitro, the presence of prostate tumors and for treating such tumors, especially once the tumors have metastasized.

Various monoclonal antibodies to prostate antigenic markers have been previously described. These previously-described monoclonal antibodies bind to either prostate-specific antigen (PSA) (Wang, M.C. et al, Urol., 17:159–169 (1979)), specifically incorporated herein by reference, or prostatic acid phosphatase (PAP) (Chu, T.M. et al, Urol., 15:319–322 (1978)), specifically incorporated herein by reference, or both. These previously-described monoclonal antibodies are disadvantageous because they fail to bind to some prostate tumors.

SUMMARY OF THE INVENTION

Accordingly, it is an object of the present invention to provide monoclonal antibodies having binding specificity to human prostate tumor-associated antigens but which do not bind to PSA or PAP.

Another object of the present invention is to provide monoclonal antibodies which bind to antigens associated with all prostate tumors and have little or no binding to cells originating from organs other than the prostate.

An additional object of the present invention is to provide methods for diagnosing prostate tumors and metastases thereof employing these monoclonal antibodies.

A further object of the present invention is to provide methods of treatment of prostate tumors and metastases thereof employing these monoclonal antibodies.

Additional objects and advantages of the present invention will be apparent from the detailed description of the invention provided hereinafter.

DETAILED DESCRIPTION OF THE INVENTION

Figure 1A:
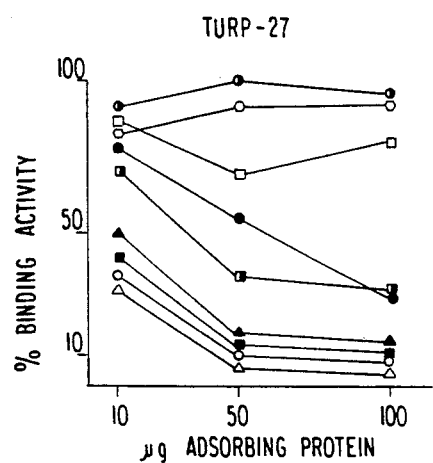
FIGS. 1A and 1B graphically illustrate the quantitative absorption of monoclonal antibodies TURP-27 and TURP-73, respectively, with crude membrane preparations of human tissues.

In one embodiment, the above-described objects have been met by monoclonal antibodies having binding specificity to human prostate tumor-associated antigens but do not have binding specificity to prostate-specific antigen or prostatic acid phosphatase. Two examples of these monoclonal antibodies, which have been developed using procedures described in detail below, have been designated as TURP-27 and TURP-73 TURP-27 and TURP-73 have been deposited at the American Type Culture Collection, Rockville, Md., under Accession Nos. 40292 and 40293, respectively. The TURP-27 hybridoma is deposited at the ATCC under Accession No. HB 8977.

Each of monoclonal antibodies TURP-27 and TURP-73, which do not cross-react with the same antigens, is directed to a unique epitope present on malignant prostate tissue. In addition, each, to a varying, although clinically acceptable degree, is organ-specific or organ-associated for prostate tissues. Thus, these new monoclonal antibodies are useful for diagnosing the presence of prostatic tumors and metastases thereof and for treating the same.

In another embodiment, the above-described objects of the present invention have been met by a method for diagnosing prostate tumors or metastases comprising:

(a) obtaining a sample of body fluid from a patient;

(b) exposing the body fluid to a monoclonal antibody having binding specificity to human prostate tumor-associated antigens but not having binding specificity to prostate-specific antigen or prostatic acid phosphatase;

(c) determining the amount of monoclonal antibody binding to substances present in the body fluid: and (d) comparing the amount of monoclonal antibody bound to body fluid substances to a predetermined base level to ascertain the presence of prostate tumors or metastases thereof.

In still another embodiment, the above-described objects of the present invention have been met by a method for diagnosing the presence of prostate tumors or metastases thereof comprising:

(a) administering, to a patient, a monoclonal antibody having binding specificity to human prostatic tumor-associated antigens but not having binding specificity to prostate-specific antigen or prostatic acid phosphatase, wherein said monoclonal antibody is conjugated to a marker; and (b) exposing the patient to a detection device to identify areas of marker corresponding to prostate tumor sites or metastatic sites thereof.

In a still further embodiment, the above-described objects of the present invention have been met by a method of treatment of a patient afflicted with a prostate tumor or metastases thereof comprising administering to said patient, a pharmaceutically effective amount of a monoclonal antibody-therapeutic agent, wherein said monoclonal antibody has binding specificity to human prostate-associated antigens but not having binding specificity to prostate-specific antigen or prostatic acid phosphatase.

According to the present invention, monoclonal antibodies having binding specificity to human prostate tumor-associated antigens but not having binding specificity to PSA or PAP can be produced and isolated as follows.

Mice are immunized with prostate tumor preparations. The spleen cells from immunized mice are isolated and fused with mouse myeloma cells and cultured under conditions which allow only for growth of hybridomas The hybridomas are then screened for production of the desired monoclonal antibody.

Immunization of mice, isolation of the immunized cells, fusion of the isolated cells with mouse myeloma cells and culturing under conditions which allow for growth of hybridomas are all conducted by methods well known or readily determined by those skilled in the art.

For immunization of the mouse spleen cells, a preparation from any tumor having prostate tumor-associated antigens can be used. Preferred tumor preparations include those from benign prostatic hyperplasias and prostate carcinomas, particularly prostate adenocarcinomas.

Further, immunization can be carried out with a preparation from just one tumor or from a mixture of one or more tumors comprising one or more tumor types. In this respect, an especially preferred preparation consists of a mixture of three benign prostatic hyperplasias and one prostate adenocarcinoma.

The mouse myeloma cell line can be any of a number of readily available to those skilled in the art. An especially preferred well known and readily available mouse myeloma cell line is P3-NS-1-Ag4-1 (obtained from NIGMS Human Genetic Mutant Cell Repository, repository number GM3573) (NS-1)).

Screening for production of the desired monoclonal antibody is accomplished by determining restricted binding activity to prostate antigens, i.e., binding to prostatic tumor-associated antigens but not to PSA or PAP, and by the lack of cross-reactivity to normal antigens, including those from normal bladder, breast, colon, kidney, lung, pancreas and liver. To be clinically acceptable, the monoclonal antibody must lack reactivity to PSA and PAP and desirably entirely lack cross-reactivity to non-prostate normal antigens. However, the monoclonal antibody can have some reactivity to non-prostate normal antigens if the antigen is from tissue unrelated to the use of the monoclonal antibody in the clinical application. Assays for restricted binding activity to prostate antigens and cross-reactivity to non-prostate normal antigens are readily determined by those skilled in the art.

The monoclonal antibodies are produced in large quantities by injecting hybridoma cells producing the monoclonal antibodies into the peritoneal cavity of mice, and after an appropriate time, harvesting ascites fluid from the mice which yields a very high titer of homogenous antibody and isolating the monoclonal antibodies therefrom. Alternatively, the antibodies can be produced by culturing monoclonal antibody producing cells in vitro and isolating secreted monoclonal antibodies from the cell culture medium.

Hybridomas expressing monoclonal antibodies designated TURP-27 and TURP-73 were produced according to the above method. The binding specificity of these two monoclonal antibodies and a comparison of such with known prostate monoclonal antibodies are discussed in more detail in Example 1 below.

Another embodiment of the present invention involves an in vitro method for diagnosing prostate tumors or matastases.

As described above, a body fluid is obtained from a patient and exposed to the monoclonal antibody of the present invention. The diagnosis is then made by determining the amount of monoclonal antibody binding to substances present in the body fluid and comparing the amount of monoclonal antibody bound to the body fluid substances to a predetermined base level. An amount of bound monoclonal antibody exceeding the base level indicates the likely presence of a prostate tumor or metastases thereof.

The body fluid which can be used in the in vitro method is any body fluid suspected of containing human prostate tumor-associated antigens. Examples thereof include blood, serum, seminal plasma, semen, urine and prostatic fluid. The body fluids can be obtained by methods readily known to or determined by those skilled in the art.

The body fluid is exposed to the monoclonal antibody and the amount of monoclonal antibody bound to substances in the body fluid is determined by means of immunochemical assays well known to those skilled in the art, as described, for example, in Klug, T.L. et al, *Cancer Res.*, 44:1048 (1984), Herlyn, M. et al, *J. Clin. Immunol.*, 2:135 (1982), Metzgar, R.S. et al, *Proc. Natl. Acad. Sci., USA.* 81:5242 (1984), Papsidero, L.D. et al, *Cancer Res.*, 44:4653 (1984), Hayes, D.F. et al, *J. Clin.*

*Invest.*, 75:1671 (1985), Killian, C.S. et al, *J. Natl. Cancer Inst.*, 76:179 (1986), Killian, C.S. et al, *Cancer Res.*, 45:886 (1985), Hedin, A. et al, *Proc. Natl. Acad. Sci., USA.* 80:3470 (1983), Pekary, A.E. et al, *Clin. Chem.*, 30:1213-1215 (1984), Bast, R.C. et al, *New England J. Med.*, 309:883-887 (1983) and Bellet, D.H. et al, *Proc. Natl. Acad. Sci., USA,* 81:3869-3873 (1984), all of which are specifically incorporated herein by reference.

Examples of suitable well known immunochemical assays include "sandwich" or "two-site" immunoradiometric assays, competitive binding assays such as radioimmunoassays, and enzyme immunoassays, which can use enzyme agents capable of being detected spectrophometrically or spectrofluorometrically.

As an example of one type of immunochemical assay useful in the present invention, is a sandwich immunoradiometric assay (IRMA) in which antigen is measured directly by reacting it with an excess of labelled antibody. In such assays, before the antigen is reacted with labelled antibody, it is insolubilized on an immunoadsorbent which specifically binds the antigen. The immunoadsorbent is formed by affixing a monoclonal antibody of the present invention. In sandwich assays for an antigen which is monomeric, two antibodies which recognize distinct epitopes on the antigen are required so that there is no competition for binding to antigen. One is used to form the immunoadsorbent; the other is used as the labelled tracer. In assays for dimeric or polymeric antigens, the same antibody can be used to form the immunoadsorbent as the labelled tracer.

Sandwich IRMA's may be performed in forward, reverse or simultaneous mode.

In a forward sandwich assay for human prostate tumor-associated antigens, a monoclonal antibody of the present invention is affixed to a solid phase to form an immunoadsorbent specific for human prostrate tumor-associated antigens. A liquid sample containing human prostate tumor-associated antigens is incubated with the immunoadsorbent. Incubation is maintained for a sufficient period of time to allow the human prostate tumor-associated antigens in the liquid sample to bind the immobilized monoclonal antibody on the immunoadsorbent. After this first incubation, the solid phase immunoadsorbent is separated from the incubation mixture. The immunoadsorbent may be washed to remove unbound interferring substances, such as non-specific binding proteins, which may also be present in the liquid sample The immunoadsorbent containing human prostate tumor-associated antigens bound to immobilized monoclonal antibody is subsequently incubated with labelled monoclonal antibody of the present invention. Again, the incubation is carried out for a period of time and under conditions sufficient to ensure binding of the labelled antibody to the human prostate tumor-associated antigen. After the second incubation, another wash may be performed to remove unbound labelled antibody from the solid phase immunoadsorbent. The labelled antibody bound to the solid phase immunoadsorbent is then measured, and the amount of labelled antibody detected serves as a direct measure of the amount of human prostate tumor-associated antigen.

The sandwich IRMA may also be performed in reverse and simultaneous modes. In reverse mode, an incubation mixture is formed of the liquid sample to be tested and a soluble labelled antibody directed against human prostate tumor-associated antigens. The mixture is incubated, then contacted with a solid phase immunoadsorbent also containing a monoclonal antibody directed against human prostate tumor-associated antigens. After another incubation, the immunoadsorbent is separated from the mixture and the label bound to the immunoadsorbent is taken as an indication of the amount of human prostate tumor-associated antigen in the liquid sample.

In the simultaneous mode, an incubation mixture is formed of the liquid sample, the labelled monoclonal antibody and the solid phase immunoadsorbent. After appropriate incubation, the solid phase immunoadsorbent is separated from the mixture and the label associated with the immunoadsorbent is measured to give an indication of the amount of human prostate tumor-associated antigens in the liquid sample.

For each incubation step in the various formats of the assays, the time and conditions of incubation are selected to ensure maximal binding of human prostate tumor-associated antigens to the immobilized antibody and to labelled antibody.

In addition to the IRMA's described herein, other immunoassays useful in this invention include competitive binding assays such as radioimmunoassays (RIA). One suitable type of RIA is a solid phase RIA.

A solid phase immunoadsorbent is prepared as described for the IRMA.

The immunoadsorbent is then incubated with the liquid sample and a known amount of labelled human prostate tumor-associated antigen for a period of time and under conditions which permit binding of the human prostate tumor-associated antigen to the immunoadsorbent. The immunoadsorbent is separated from the liquid sample and the amount of label associated therewith is assessed. By reference to a pre-established inhibition curve defining the relationship between labelled human prostate tumor-associated antigen associated with the immunoadsorbent, the amount of unlabelled human prostate tumor-associated antigen in the liquid sample is determined.

In the various solid phase assays, the immunoadsorbent is separated from incubation mixtures containing the liquid sample, the labelled antibody or both. Separation can be accomplished by any conventional separation technique such as sedimentation or centrifugation. Preferably, though not necessarily, the immunoadsorbent is washed prior to contacting it, when required, with a second incubation medium and prior to measuring the amount of label associated with the immunoadsorbent. The washing removes non-specific interferring substances or excess labelled antibody which may affect the accuracy and sensitivity of the assay.

As the last step in the in vitro diagnostic method according to the present invention, the amount of monoclonal antibody binding to substances present in the body fluid is compared to a predetermined base level.

The determination of the base level of monoclonal antibody assay binding to be expected is a determination routinely made by those of ordinary skill in the art when defining the parameters necessary for reading of a diagnostic test of this sort. These determinations may be made without undue experimentation, particularly in light of the teachings set forth herein.

Generally, the "base level" is defined as (1) two standard deviations above the mean of the normal population, or (2) the level below which 99% of the normal population falls.

In a third embodiment of the present invention, a method for in vivo diagnosis of prostate tumors or matastases thereof is provided.

The method involves administering to a patient a monoclonal antibody of the present invention conjugated to a marker and then detecting the presence of the marker in the patient by exposing the patient to an appropriate detecting device.

Administration and detection of the monoclonal antibody conjugated to a marker as well as methods of conjugation of the antibody to the marker are accomplished by methods readily known to or readily determined by those skilled in the art. See for example, Goldenberg, D.M. et al, *New England J. Med.*, 298:1384–1388 (1978), Goldenberg, D.M. et al, *J. A. M. A.*, 250:630–635 (1983), Goldenberg. D.M. et al, *Gastroenterol.*, 84:524–532 (1983), Siccardi, A.G. et al, *Cancer Res.*, 46:4817–4822 (1986). Epenetos, A.A. et al, *Cancer,* 55:984–987 (1985), Philben, V.J. et al, *Cancer,* 57:571–576 (1986), Chiou, R. et al, *Cancer Res.*, 45:6140–6146 (1985) and Hwang, K.M. et al, *J. Natl. Cancer Inst.*, 76:849–855 (1986), all of which are specifically incorporated herein by reference.

The dosage will vary depending upon the age and weight of the patient, but generally a one time dosage of about 0.1 to 20 mg (of the monoclonal antibody conjugated to a marker) per patient is sufficient. A more preferred dosage is about 1.0 to 2.0 mg (of the monoclonal antibody conjugated to a marker) per patient.

Examples of markers which can be conjugated to the antibody are well known to those skilled in the art and include substances which can be detected by nuclear magnetic resonance imaging, i.e., nuclear magnetic spin-resonance isotopes, and radioactive substances.

A preferred example of a nuclear magnetic spin-resonance isotope is gadolinium (Gd).

Suitable examples of radioactive markers include $I^{125}$, $I^{131}$, $I^{123}$, $In^{111}$, $In^{113}$, $Ga^{67}$, $Ga^{68}$, $Ru^{97}$, $Ru^{103}$, $Hg^{197}$, $Hg^{203}$, and $Tc^{99m}$. $In^{111}$ and $Tc^{99M}$ are preferred due to their low energy and suitability for long range detection.

Detection of radioactive markers is by means of a gamma scintillation camera or the like as described in the references cited above.

Nuclear magnetic imaging devices can be used to detect nuclear magnetic spin-resonance isotope markers.

In a fourth embodiment, the present invention provides a method of treatment of a patient afflicted with a prostate tumor or metastases thereof.

The method involves administering to a patient a pharmaceutically effective amount of a monoclonal antibody-therapeutic agent, wherein the monoclonal antibody is one according to the present invention.

Methods of preparing and administering the monoclonal antibody-therapeutic agent as well as suitable dosages are well known to or readily determined by those skilled in the art. Representative protocols are described in the references cited below.

Examples of the monoclonal antibody-therapeutic agents used in therapy include antibodies coupled to drugs such as methotrexate and adriamycin as described in, for example, Deguchi, T. et al, *Cancer Res.*, 46:3751 (1986), Deguchi, T. et al, *Fed, Proc.*, 44:1684 (1985), Embleton, M.J. et al, *Br. J. Cancer,* 49:559 (1984) and Pimm, M.V. et al, *Cancer Immunol. Immunother.*, 12:125–134 (1982), all of which are specifically incorporated herein by reference; antibodies coupled to toxins, as described in, for example, Uhr, J.W. et al, *Monoclonal Antibodies and Cancer,* Academic Press, Inc., pp. 85–98 (1983), Vitetta, E.S. et al, *Biotechnology and Biol. Frontiers,* Ed. P.H. Abelson, pp. 73–85 (1984) and Vitetta, E.S. et al, *Sci.,* 219:644–650 (1983), all of which are specifically incorporated herein by reference; antibodies coupled to isotopes, such as $I^{131}$, $Yt^{90}$, $Sc^{47}$, $Cu^{67}$, $Bi^{212}$, $Pb^{212}$ and $At^{211}$, as described in, for example, Goldenberg, D.M. et al, *Cancer Res.*, 41:4353 (1981), Carrasquillo, J.A. et al, *Cancer Treat. Rep.*, 68:317 (1984), Zalcberg, J.R. et al, *J. Natl. Cancer Inst.*, 72:697 (1984), Jones, D.H. et al, *Int. J. Cancer,* 35:715 (1985), Lange, P.H. et al, *Surgery,* 98:143 (1985), Kaltovich, F.A. et al, *J. Nucl. Med.*, 27:897 (1986), Order, S.E. et al, *Int. J. Radiother. Oncol. Biol. Phys.*, 8:121 (1982), Courtenay-Luck, N. et al, *Lancet,* 1:1441 (1984) and Ettinger, D.S. et al, *Cancer Treat. Rep.*, 66:289–297 (1982), all of which are specifically incorporated herein by reference; heterobifunctional antibodies, for example, antibodies coupled or spliced to another antibody so that the complex binds both to the tumor and the body's own killer cells such as T cells, as described, for example, in Perez, P. et al, *J. Exper. Med.*, 163:166–178 (1986) and Lau, M.A. et al, *Proc. Natl. Acad. Sci., USA,* 82:8648–8652 (1985), both of which are specifically incorporated herein by reference; and native, i.e., non-conjugated or non-complexed, antibody, as described in, for example, Herlyn, D. et al, *Proc. Natl. Acad. Sci., USA.,* 79:4761 (1982), Schulz, G. et al, *Proc. Natl. Acad. Sci., USA,* 80:5407 (1983), Capone, P.M. et al, *Proc. Natl. Acad. Sci., USA,* 80:7328 (1983), Sears, H.F. et al, *Cancer Res.*, 45:5910 (1985), Nepom, G.T. et al, *Proc. Natl. Acad. Sci., USA,* 81:2864 (1984), Koprowski, H. et al, *Proc. Natl. Acad. Sci., USA,* 81:216 (1984) and Houghton, A.N. et al, *Proc. Natl. Acad. Sci., USA,* 82:1242 (1985), all of which are specifically incorporated herein by reference.

In this embodiment of the invention, the monoclonal antibody-therapeutic agent can be delivered directly to the tumor site thereby directly exposing the tumor tissue to the therapeutic agent.

The following examples are provided for illustrative purposes only and are in no way intended to limit the scope of the present invention.

EXAMPLE 1

Production of Monoclonal Antibodies TURP-27 and TURP-73

(A) Production of Hybridomas

Three female BALB/c mice (Harlan Sprague-Dawley, Indianapolis, IN, 20-week-old) were hyperimmunized against a crude membrane antigen preparation derived from a pool of three benign prostatic hyperplasia (BPH) specimens and one prostate adenocarcinoma transurethral resection specimen.

The crude membrane antigen preparation was prepared by incubating single cell suspensions for 1 to 2 hours in hypotonic buffer comprising 20 mM Hepes (pH 7.1), 5.0 mM NaCl, 1.0 mM $MgCl_2$, 0.1 M NaF and 2.0 mM PMSF. The cells were then lysed by Dounce homogenization. The nuclear fraction was removed by centrifugation at a200×g for 5 minutes, and the supernatant was decanted and recentrifuged at 25,000×g for 30 minutes at 4° C. The resulting pellet was then redissolved in 1.5 ml of a 37% (v/v) sucrose solution in membrane buffer comprising 20 mM Hepes (pH 6.8), 40 mM NaCl, 0.1 mM EDTA and 2.0 mM PMSF, overlaid with 3.0 ml of a 20% (v/v) sucrose solution in membrane buffer and centrifuged at 2,000 rpm for 16 hours at 2° C. The membrane rich (20-37%) interface was then removed in approximately 1.0 ml. diluted with 10 ml of membrane buffer and centrifuged at 40,000 rpm for 2 hours at 10° C. to obtain the crude membrane antigen preparation.

The mice were immunized (day 0) subcutaneously (0.1 ml) and intramuscularly (0.05 ml in rear flanks) with 100 μg of the crude membrane antigen preparation mixed with an equal volume of complete Freund's adjuvant. The mice were boosted with intraperitoneal injections of 100 μg of the crude membrane antigen preparation in 0.1 ml PBS on days 6 and 36. On day 66, the mice were given an intravenous injection of 100 μg of the crude membrane antigen preparation in 0.1 ml PBS and the spleens were removed for fusion four days later. Spleen cells from the hyperimmunized mice were fused with P3-NS-1-Ag4-1 mouse myeloma cells as described by Kohler, G. et al, in *Eur. J. Immunol.*, 6:292-295 (1976), specifically incorporated herein by reference, in the presence of 50% polyethylene glycol (American Type Culture Collection, 1300-1600 MW) according to procedures established by Koprowski, H. et al, *Proc. Natl. Acad. Sci. USA*, 74:2985-2988 (1977). specifically incorporated herein by reference. After fusion, the cells ($3.0 \times 10^8$ spleen and $3.0 \times 10^7$ myeloma) were washed and resuspended in 300 ml of HSI LoSM medium (Hybridoma Sciences, Inc., Atlanta, Ga.) medium containing 10% (v/v) fetal bovine serum (Hyclone Laboratories, Logan. Utah), $1.0 \times 10^{-4}$ M hypoxanthine, $4.0 \times 10^{-7}$ M aminopterin, $6.4 \times 10^{-5}$ M thymidine, and 50 μg/ml gentamicin (Grand Island Biological Co., Grand Island, N.Y.). The cells were then dispersed in 96-well microtiter plates (Costar, Cambridge, Mass.) in 0.2 ml aliquots. Hybridomas that were determined to be of interest, i.e., that produced monoclonal antibodies having binding specificity to prostate antigens but not to non-prostate antigens, were doubly cloned by limiting dilution. In this manner, two hybridomas producing monoclonal antibodies designated as TURP-27 and TURP-73 were developed. TURP-27 and TURP-73 have been deposited at the American Type Culture Collection, Rockville, Md. under ATCC Nos. 40292 and 40293, respectively. The TURP-27 hybridoma is deposited at the ATCC under Accession No. HB 8977.

(B) Screening of Hybridoma Supernatants

Supernatants from actively growing hybridomas were screened for binding activity against a number of normal, hyperplastic, virally-transformed, and malignant cell lines (Starling, J.J. et al, *Cancer Res.*, 42:3084-3089 (1982)), specifically incorporated herein by reference, and crude membrane extracts using a solid-phase RIA as described by Starling, J.J. et al, *J. Supramol. Struct.* 11:563-577 (1979), specifically incorporated herein by reference.

The monoclonal antibodies were used as culture supernatants from hybridomas grown in the presence of 10% (v/v) fetal calf serum under standard culture conditions. The protein concentration was determined by the method of Lowry, O.H. et al, *J. Biol. Chem.* 193:265-275 (1951), specifically incorporated herein by reference. The culture supernatants were found to contain approximately 15 to 30 μg monoclonal antibody/ml.

Whole cells or crude membrane extracts were attached by glutaraldehyde fixation to individual wells of 96-well polyvinylchloride microtiter plates (Dynatech Laboratories, Inc., Alexandria, Va.). More specifically, whole cells or crude membrane extracts 3.0 μg/well were added to each well and the wells were dried. Then, 0.1% (v/v) glutaraldehyde was added to each well for a few minutes and washed with PBS. The fixed cells were incubated with the hybridoma culture supernatants for 1 hour at room temperature. After extensive washing, 25 ml of affinity-purified (Guimezanes, A. et al, *Eur. J. Immun.*, 6:69-72 (1976)), specifically incorporated herein by reference, $^{125}$I-labelled (Hunter, R., *Proc. Soc. Biol. Med.*, 133:989-992 (1970)), specifically incorporated herein by reference, F(ab')$_2$ fragments (Fridman, W.H. et al, Cell Immun., 11:442-445 (1974)), specifically incorporated herein by reference, of rabbit anti-mouse IgG serum (Miles Laboratories, Elkhardt, Ind.) were added to each well (100,000 cpm) for 1 hour. The plate was washed, and individual wells were cut out of the flexible microtiter plate and were counted in a gamma counter. The results are shown in Tables 1 and 2 below.

TABLE 1

Binding of Monoclonal Antibodies TURP-27 and TURP-73 to Human Cell Lines in Solid-Phase RIA

| Cell Lines | Origin | Binding Ratio 27 | 73[a] |
|---|---|---|---|
| Prostate Carcinoma | | | |
| DU145 | brain metastasis | 1.6 | 4.0 |
| PC-3 | bone metastasis | 2.1 | 5.8 |
| LNCaP | lymph node metastasis | 0.9 | 3.4 |
| Bladder Carcinoma | | | |
| 253 J | lymph node metastasis | 1.2 | 1.5 |
| T-24 | primary | 1.5 | 2.1 |
| 639V | primary | 1.6 | 0.9 |
| Melanoma | | | |
| WM-9 | lymph node metastasis | 1.0 | 1.3 |
| H1477 | primary | 1.2 | 2.1 |
| Pancreatic Carcinoma | | | |
| MIA | primary | 1.5 | 2.3 |
| Panc-1 | primary | 0.9 | 3.0 |
| Kidney Carcinoma | | | |
| A498 | primary | 1.5 | 2.3 |
| CaKi-2 | primary | 1.3 | 1.9 |
| Breast Carcinoma | | | |
| ZR-75-1 | ascites | 1.3 | 7.0 |
| BT-20 | primary | 0.7 | 1.8 |
| Colorectal Carcinoma | | | |
| SW 1116 | primary | 1.0 | 8.9 |
| CX-1 | primary | 1.3 | 11.4 |
| Leukemia | | | |
| MOLT-3 | T cell | 1.2 | 1.9 |
| CCRF-SB | B cell | 1.5 | 1.5 |
| Lymphoma | | | |
| Raji | Burkitt | 2.1 | 1.8 |
| U937 | histocytic | 1.9 | 1.9 |
| Virally-transformed | | | |
| CMV-Mj-HEL-1 | cytomegalovirus | 0.9 | 1.0 |
| Normal fibroblasts | | | |
| WI-38 | lung | 1.1 | 1.2 |
| Flow 4000 | kidney | 2.0 | 2.5 |
| GM-10 | skin | 1.0 | 1.6 |

[a]Binding ratio represents the total number of cell-bound counts using hybridoma culture supernatant divided by the number of cell-bound counts using the P3X63/Ag8 myeloma (ATCC No. TIB 9) supernatant which contains the MOPC 21 IgG . Reactions are scored positive if the binding ratio is greater than 3. The results are the average of duplicate determinations with less than 20% variance between wells for any one test.

TABLE 2

Binding of Monoclonal Antibodies TURP-27 and TURP-73 To Human Tissue Membrane Preparations in a Solid-Phase RIA

| | | Binding Ratio | |
|---|---|---|---|
| Specimen[b] | Tissue Type | 27 | 73[a] |
| Ca 1046 | prostate carcinoma | 6.4 | 5.7 |
| Ca 1124 | prostate carcinoma | 8.4 | 22.5 |
| Ca 1126 | prostate carcinoma | 9.6 | 18.4 |
| Ca 1129 | prostate carcinoma | 4.0 | 13.8 |
| Ca 1122 | BPH | 17.4 | 6.6 |
| P-5-80 | BPH | 5.7 | 25.8 |
| P-125-80 | BPH | 1.4 | 8.0 |
| P-144-80 | BPH | 11.4 | 19.3 |
| P-151-80 | BPH | 21.1 | 55.2 |
| P-8-80 | normal prostate | 1.0 | 7.1 |
| P-16-80 | normal prostate | 1.8 | 10.5 |
| P-104-80 | normal prostate | 1.3 | 6.7 |
| P-108-80 | normal prostate | 1.6 | 7.7 |
| P-110-80 | normal prostate | 1.9 | 13.8 |
| P-117-80 | normal prostate | 4.0 | 9.1 |
| P-119-80 | normal prostate | 1.0 | 9.1 |
| TURP[c] | prostate carcinoma, BPH | 4.3 | 13.0 |
| Ca 1101 | normal bladder | 1.4 | 2.8 |
| Ca 1037 | normal bladder | 1.7 | 1.9 |
| Ca 1037 | normal ovary | 1.3 | 1.1 |
| Ca 1030 | normal ovary | 1.0 | 1.0 |
| Ca 1005 | normal colon | 2.1 | 1.6 |
| Ca 1030 | normal colon | 1.8 | 1.3 |
| Ca 1037 | normal kidney | 1.9 | 10.8 |
| Ca 1042 | normal kidney | 1.8 | 11.5 |
| Ca 1013 | normal liver | 2.5 | 1.6 |
| Ca 1026 | normal liver | 1.7 | 1.2 |
| Ca 1030 | normal lymph node | 2.2 | 1.4 |
| Ca 1030 | normal pancreas | 2.3 | 2.8 |
| Ca 1008 | normal spleen | 2.1 | 1.7 |
| Ca 1028 | normal spleen | 2.3 | 1.8 |
| Ca 1028 | normal testicle | 1.8 | 1.1 |
| Ca 1043 | normal testicle | 2.1 | 1.7 |
| Ca 1031 | normal ureter | 2.4 | 1.6 |
| Ca 1037 | normal breast | 3.0 | 1.9 |

[a]See footnote "a" in Table 1.
[b]Surgical and autopsy specimens were assigned identification numbers to maintain confidentiality. Specimens were stored at −70° C. until utilized for crude membrane preparations.
[c]Pooled BPH and prostrate carcinoma specimens were used as immunogen for hybridoma production.

As the results in Tables 1 and 2 above demonstrate, the monoclonal antibody designated as TURP-27 was not reactive against any of the human cell lines tested (Table 1) but did bind to four of four prostate adenocarcinomas, four of five BPH and one of seven normal prostate membrane preparations (Table 2). TURP-27 also did not react with any other normal tissues examined in the RIA including bladder, ovary, colon, kidney, liver, lymph node, pancreas, spleen, testicle, ureter, and breast (Table 2).

On the other hand the monoclonal antibody designated as TURP-73 exhibited a reactivity to a wider range of cell lines and tissues. Specifically, TURP-73 bound to the three well-characterized human prostate adenocarcinoma cell lines (DU145, PC-3, LNCaP) as well as to the ZR-75-1 breast carcinoma and the SW1116 and CX-1 colorectal carcinoma cell lines (Table 1). TURP-73 also reacted strongly to all normal, benign hyperplastic, and malignant prostate membrane preparations tested and also bound to normal kidney (Table 2).

(C) Immunofluorescent Staining

Immunofluorescence of live and fixed cells was performed as described in Starling, J.J. et al, *Cancer Res.*, 42:3084-3089 (1982) and Starling, J.J. et al, *Cancer Res.*, 45:804-808 (1985), both of which are specifically incorporated herein by reference.

More specifically, $10^6$ cells were placed in plastic tubes and washed twice with cold PBS. The cell pellets were resuspended in 100 μl of hybridoma culture supernatant and incubated for 30 minutes at 4° C. The cell pellets were washed twice with cold PBS and then mixed with 25 ml of a 1120 dilution of fluorescein isothiocyanate-conjugated anti-mouse IgG (heavy and light chain specific; Cappel Laboratories, Cochranville, Pa.) and incubated for 30 minutes at 4° C. The cells were washed twice more in cold PBS and stored on ice until ready to view. Wet mounts of cell suspensions were made as soon as possible and examined with a Zeiss fluorescent microscope. The number of cells showing positive fluorescence out of 300 total cells were counted to determine the percentage of the cells exhibiting fluorescence.

TURP-27 was not found to bind by immunofluorescence, to live or methanol:acetic acid-, formalin- or ethanol-fixed DU145 or PC-3 cells confirming the non-reactivity of this monoclonal antibody to prostate tumor cell lines which was observed by RIA. On the other hand, TURP-73 was found to provide a strong membrane fluorescence of PC-3 cells that persisted following alcohol or formalin fixation.

(D) Quantitative Absorption

Monoclonal antibody absorption analyses utilizing crude membrane antigen preparations or whole cells were performed as described in Starling, J.J. et al, *Cancer Res.*, 42:3084-3089 (1982), specifically incorporated herein by reference, and protein determinations were carried out by the method of Lowry, O.H. et al, *J. Biol. Chem.*, 193:265-275 (1951), specifically incorporated herein by reference. Dilutions (1:10 and 1:500) of culture supernatants from TURP-27 and TURP-73 were used, respectively. Varying amounts of crude membrane antigen preparations were added and the final volume was 0.11 ml. The assay was performed as described by Wright, G.L. et al, *Urol.*, 19:351-355 (1982), specifically incorporated herein by reference. The results are shown in FIGS. 1A and 1B.

Figure 1B:
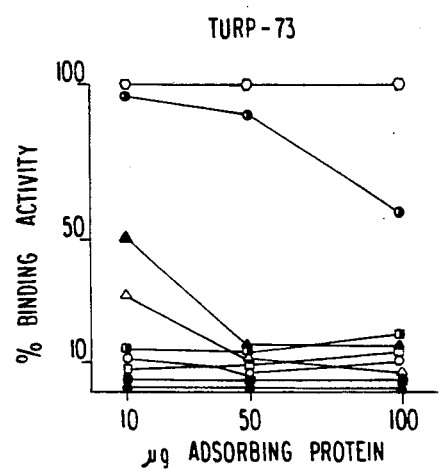

In FIGS. 1A and 1B, ● represents Ca 1124 prostate adenocarcinoma; represents Ca 1126 prostate adenocarcinoma; ▲ represents P-144-80 benign prostatic hyperplasia; Δ represents P-151-80 benign prostatic hyperplasia; ○ represents Ca-1122 benign prostatic hyperplasia; □ represents P-16-80 normal prostate; ■ represents P-117-80 normal prostate; represents Ca 1026 normal liver; and ◑ represents Ca 1005 normal colon. In FIGS. 1A and 1B, the percentage of binding activity is defined as follows:

$$100 \times \frac{(a - b)}{(c - d)}$$

wherein a is the cpm of the adsorbed monoclonal antibody; b is the cpm of P3X63/Ag8 myeloma MOPC 21 IgG1 control monoclonal antibody and c is the cpm of the unadsorbed monoclonal antibody. The target antigen employed was Ca 1124 prostate adenocarcinoma membrane preparation.

FIGS. 1A and 1B demonstrate that TURP-27 was not reactive with tissues which had no apparent binding activity in the RIA (normal liver, normal colon, normal prostate P16-80) while tissues that did react in the RIA (Table 2) also demonstrated significant absorption activity for TURP-27. TURP-73 exhibited a similar pattern although some absorption was observed with high levels of a normal colon membrane extract (Ca 1005) which was not reactive with TURP-73 in the RIA (Table 2).

It was also found that absorption of TURP-27 with $10^7$ DU145, PC-3 or LNCaP cells or 100 μg of cell protein extracts of these prostate tumor lines failed to reduce the binding of this monoclonal antibody to the Ca 1126 prostate carcinoma target antigen; whereas, it was found that 50-85% of the binding of TURP-73 to the target antigen was reduced by either whole cells or cell lysates.

(E) Immunohistochemistry

The binding specificity of TURP-27 and TURP-73 was also evaluated using an immunoperoxidase assay. Avidin-biotin immunoperoxidase analyses were performed on formalin-fixed, paraffin-embedded tissues using the ABC Vectastin kit (Vector Laboratories, Burlingame, Calif.) as described by Wright, G.L. et al, Cancer Res., 43:5509-5516 (1983), specifically incorporated herein by reference. The results are set forth in Table 3 below.

TABLE 3

Immunoperoxidase Staining of Normal, Benign Hyperplastic And Cancerous Human Tissue With Monoclonal Antibodies TURP-27 and TURP-73[a]

| Tissue Source | Tissue Type | Monoclonal Antibodies | |
|---|---|---|---|
| | | 27 | 73 |
| Prostate | Primary carcinoma | 11/11 | 11/11 |
| | Metastatic carinoma[b] | 6/6 | 3/5 |
| | BPH | 6/6 | 6/6 |
| | Normal[c] | 3/3 | 3/3 |
| Bladder | Primary carcinoma | 0/6 | 0/6 |
| | Normal | 0/6 | 0/6 |
| Breast | Primary carcinoma | 0/6 | 0/6 |
| | Normal | 3/6[d] | 0/6 |
| Colon | Primary carcinoma | 0/6 | 2/6 |
| | Normal | 0/6 | 0/6 |
| Kidney | Primary carcinoma | 0/6 | 0/6 |
| | Normal | 0/6 | 5/6[e] |
| Lung | Primary carcinoma | 0/6 | 0/6 |
| | Normal | 0/6 | 0/6 |
| Pancreas | Primary carcinoma | 0/6 | 0/6 |
| | Normal | 0/6 | 0/6 |
| Liver | Normal | 0/4 | 0/4 |

[a]Serial sections of formalin-fixed tissue were reacted with approximately 3.0 to 6.0 μg of antibody per slide.
[b]Panel consisted of five prostate adenocarcinoma lymph node metastases and one lung metastasis.
[c]Specimens obtained from young males between the ages of 18-23 with no evidence of disease based on histopathological examination. TURP-27 was reactive with a few cells in less than 10% of the glandular elements within the sections.
[d]Several cells were stained within normal ducts.
[e]Proximal tubules were weakly stained in 5/6 specimens. Renal casts present in three specimens were strongly stained.

As the results in Table 3 above demonstrate, TURP-27 reacted with all prostate specimens and did not bind to normal or malignant tissues derived from bladder, colon, kidney, lung, or pancreas. TURP-27 was not reactive with six breast carcinoma specimens but did react to three of six normal breast tissue samples, although the reactivity was confined to a few cells lining some of the normal ducts. However, as discussed above, quantitative adsorption analyses failed to detect binding by the TURP-27 monoclonal antibody to these normal breast tissues. Monoclonal antibody TURP-73 also reacted with normal, benign hyperplastic, and malignant prostate tissues in the immunoperoxidase assay and to two of six colon carcinomas. Weak staining of the proximal tubules and renal casts in normal kidney specimens was also observed with TURP-73.

(F) Binding of Monoclonal Antibodies to PAP and PSA

1. Direct Binding Solid-Phase RIA

The binding activity of purified TURP-27 and TURP-73 to purified human PAP and PSA was evaluated using a direct binding solid-phase RIA against 30 ng of PAP and 150 ng of PSA dried and fixed to individual wells of polyvinylchloride microtiter plates as described above.

TURP-27 and TURP-73 were purified to 95% homogeneity from hybridomas grown in serum-free medium (HSI LoSM, supplemented with ITS premix, Collaborative Research, Inc., Lexington, Mass.) as described previously by Wright, G.L. et al, Cancer Res., 43:5509-5516 (1983), specifically incorporated herein by reference, by Protein A-Sepharose (Sigma Chemical Co., St. Louis, Mo.) affinity chromatography for TURP-73 ($IgG_{2a}$) and by precipitating the TURP-27 Tris-HCl, pH 7.2 and reconstitution in PBS according to the methods disclosed by J. J. Langone in J. Immunol. Meth., 55:277-296 (1982) and J. W. Goding in J. Immunol. Meth., 39:285-308 (1980), both of which are specifically incorporated herein by reference. The degree of purification was determined by polyacrylamide gel electrophoresis and qualitatively evaluated. The serum-free preparations were concentrated to 1 to 2.3 mg monoclonal antibody/ml.

Prostate-specific antigen (PSA) was purified from human seminal plasma according to the methods described by Wang M.C. et al, Oncol., 39:1-5 (1982), specifically incorporated herein by reference and is commercially available from Hybritech, Inc., La Jolla, Calif. Prostatic acid phosphatase is commercially available from Sigma Chemical Co.

Monoclonal antibodies to PAP and PSA were used as positive controls while MOPC 21 $IgG_1$ was used as a negative control. Monoclonal antibodies to PAP and PSA are commercially available from Hybritech, Inc., La Jolla, Calif. The results are shown in Table 4 below.

TABLE 4

Reactivity of Monoclonals TURP-27 and TURP-73 To Prostatic Acid Phosphatase (PAP) and Prostate-Specific Antigen (PSA) In A Direct Binding RIA

| Antibody[a] | Target | CPM Bound |
|---|---|---|
| Anti-PAP | PAP | 1450 |
| TURP-27 | PAP | 210 |
| TURP-73 | PAP | 165 |
| MOPC 21 | PAP | 300 |
| Anti-PSA | PSA | 16590 |
| TURP-27 | PSA | 408 |
| TURP-73 | PSA | 210 |
| MOPC 21 | PSA | 320 |

[a]Antibodies were used at concentrations of 7.0 μg/ml.

2. Blocking Radioimmunoassay

A blocking radioimmunoassay was also performed by incubating 11 μl of a 20 μg/ml concentration of each monoclonal antibody (2.0 μg/ml) in 0.11 ml final volume of PBS containing 10% (v/v) gamma globuline-free horse serum in the absence or presence of 300 ng purified PAP or 4.0 μg PSA. The human prostate adenocarcinoma membrane crude extract Ca 1126 was used at 3.0 μg/well as the target antigen. The results are shown in Table 5 below.

TABLE 5

Inhibition of Binding of TURP-27 and TURP-73 To Their Target Antigens By Purified Prostatic Acid Phosphatase (PAP) and Prostate-Specific Antigen (PSA)

| Antibody | Blocking Antigen | CPM Bound |
| --- | --- | --- |
| Anti-PAP | None | 5400 |
| Anti-PAP | PAP | 450 |
| Anti-PAP | Ca 1126[a] | 178 |
| Anti-PSA | None | 8400 |
| Anti-PSA | PSA | 1450 |
| Anti-PSA | Ca 1126 | 1204 |
| TURP-27 | None | 4200 |
| TURP-27 | PAP | 4300 |
| TURP-27 | PSA | 4000 |
| TURP-27 | Ca 1126 | 270 |
| TURP-73 | None | 8700 |
| TURP-73 | PAP | 8800 |
| TURP-73 | PSA | 7800 |
| TURP-73 | Ca 1126 | 100 |

[a]Crude membrane extract (100 μg).

The results in Tables 4 and 5 above demonstrate that TURP-27 nd TURP-73 did not bind to PAP or PSA which was absorbed and fixed to a microtiter plate in a direct binding RIA (Table 4) nor did incubation of TURP-27 and TURP-73 with the PAP or PSA diminish TURP-27 or TURP-73 binding to the target antigen in a blocking assay (Table 5).

3. Competitive Binding Assay

Competitive binding analysis was also performed by labeling 140 μg of purified monoclonal antibody TURP-27 and TURP-73 with 0.5 mCi Na $^{125}$I (ICN, Irvine, Calif.) to a specific activity of $2.5 \times 10^6$ cpm/μg for TURP-27 and $3.0 \times 10^6$ cpm/μg for TURP-73 using the Iodobead (Pierce Chemical Co., Rockford, Ill.) method as described by Markwell, M.A.K., *Anal. Biochem.*, 125:427–432 (1982), specifically incorporated herein by reference.

Varying amounts of non-radioactive monoclonal antibodies were allowed to bind to the target antigen, i.e., Ca 1126 prostate adenocarcinoma crude membrane preparation, for 1 hour at room temperature. After washing away unbound monoclonal antibody, 250,000 cpm of $^{125}$I-labelled monoclonal antibody was added for 1 hour at room temperature. Thereafter, the plate was washed and individual wells were counted in a gamma counter. The results are shown in FIGS. 2A and 2B.

Figure 2A:
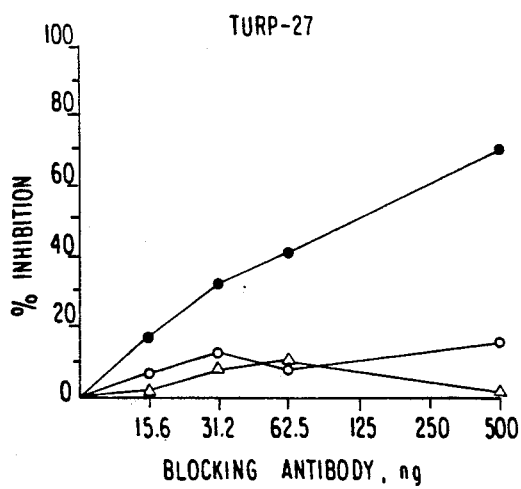
FIGS. 2A and 2B graphically illustrate the binding inhibition of $^{125}$I-labelled TURP-27 and $^{125}$I-labelled TURP-73, respectively, by unlabelled monoclonal antibodies directed against prostate antigens.
Figure 2B:
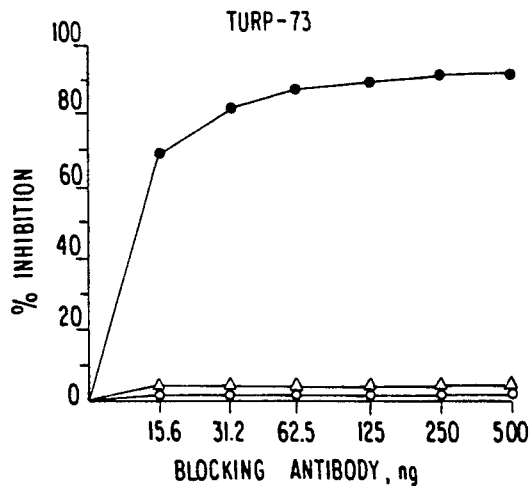

In FIGS. 2A and 2B, ○ represents inhibition of binding by monoclonal antibodies specific to PSA; Δ represents inhibition of binding by monoclonal antibodies specific to PAP and ● represents inhibition of binding by TURP-27 (FIG. 2A) or TURP-73 (FIG. 2B). In FIGS. 2A and 2B, the percentage of inhibition is defined as follows:

$$100 \times \left[ 1 - \frac{(a - b)}{(c - d)} \right]$$

wherein a is the cpm of bound $^{125}$I-labelled TURP-27 or $^{125}$I-labelled TURP-73 to Ca 1126 target antigen in the presence of blocking antibodies; b is the cpm of bound $^{125}$I-labelled TURP-27 or $^{125}$I-labelled TURP-73 to a PBS control well containing no target antigen and c is the cpm of bound $^{125}$I-labelled TURP-27 or $^{125}$I-labelled TURP-73 in the absence of blocking antibodies.

The results in FIGS. 2A and 2B demonstrate that monoclonal antibodies against PSA or PAP could not effectively block the binding of $^{125}$I-labelled TURP-27 or $^{125}$I-labelled TURP-73 to the Ca 1126 membrane target while unlabelled TURP-27 and TURP-73 were very efficient at blocking radioactive TURP-27 and TURP-73 binding, respectively.

(G) Reciprocal Binding Assay

Purified TURP-27 and TURP-73 were labeled with $^{125}$I as described above. A series of two-fold dilutions of unlabeled monoclonal antibodies were added to the target antigen (3.0 ∞g, Ca 1126) and incubated for 1 hour at room temperature. After washing $1 \times 10^6$ cpm of labeled TURP-27 or TURP-73 was added to each well and incubated for another hour at room temperature. The wells were washed and the radioactivity was counted in a gamma counter. The results are shown in FIGS. 3A and 3B.

Figure 3A:
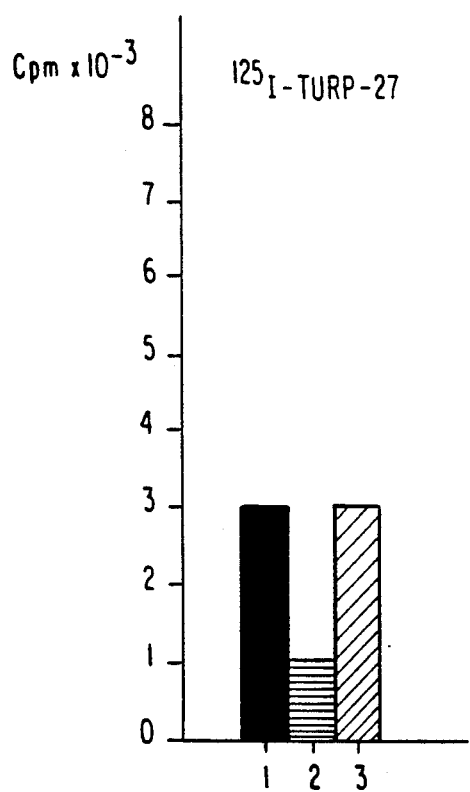
FIGS. 3A and 3B graphically illustrate cross-blocking, of binding between TURP-27 and TURP-73 respectively, to a Ca 1126 prostate carcinoma crude membrane extract antigen preparation.

In FIG. 3A, 1 represents without addition of unlabelled antibodies; 2 represents after addition of unlabelled TURP-27; and 3 represents after addition of unlabelled TURP-73. In FIG. 3B, 4 represents without addition of unlabelled antibodies; 5 represents after addition of unlabelled TURP-73; and 6 represents after addition of unlabelled TURP-27.

Figure 3B:
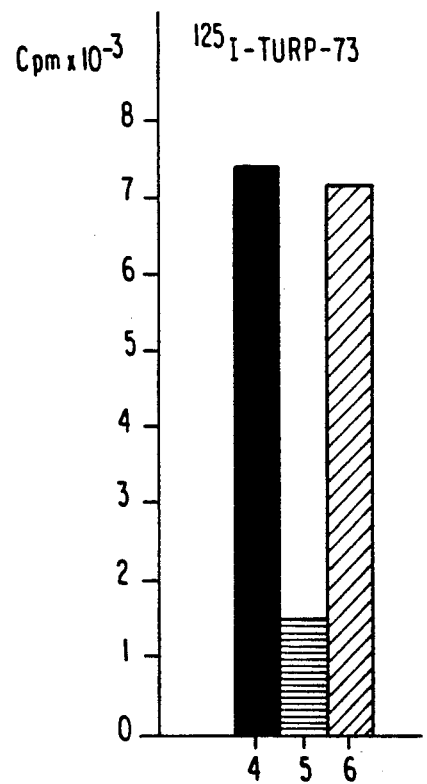

FIGS. 3A and 3B demonstrate that binding of the labeled monoclonal antibody was inhibited only by unlabeled antibodies from the autologous clone. These data demonstrate that TURP-27 and TURP-73 detect distinct antigenic determinants.

(H) Isotyping of Monoclonal Antibodies

Antibody heavy-chain and light-chain classes were determined using a mouse immunoglobulin subtype identification kit available from Boehringer-Mannheim Biochemicals, Indianapolis, Ind. TURP-27 was determined to be of the isotype $IgG_3,K$ and TURP-73 of the isotype $IgG_{2a},K$.

(I) Summary of Results

TURP-27 was not reactive to any of the human cell lines tested (Table 1) but did react to BPH and prostate adenocarcinoma tissue specimens (Tables 2 and 3). Reactivity was also observed to one of seven normal prostate membrane preparations. The prostate-specific binding activity of TURP-27 in the RIA (Table 2) was also seen in the immunoperoxidase assay except for three normal breast specimens which contained several stained cells within a few normal ducts (Table 3). Two of these breast specimens were available as frozen tissue and were utilized to make crude membrane preparations. Monoclonal antibody TURP-27 was not reactive with these specimens in the solid-phase RIA nor was any absorption activity observed with either of these tissues at concentrations as high as 100 μg absorbing protein. Substantial absorption activity was observed, however, by TURP-27-reactive samples at protein levels much lower than 100 μg (FIG. 1A).

Monoclonal antibody TURP-73 bound strongly to normal, BPH, and malignant prostate tissue as well as to colorectal carcinoma, breast carcinoma, and normal kidney specimens (Tables 1, 2, and 3). This monoclonal antibody was not widely cross-reactive to non-prostate normal or malignant cells but its antigen was present on a wider array of cell types and tissues than the TURP-27 antigen.

TURP-27 bound to one of six normal prostate membrane preparations by solid-phase RIA (Table 2). The six unreactive normal prostate specimens were from young men aged 18 to 28, while the one reactive sample was from a 66-year-old male. Due to the high incidence in prostate of occult hyperplasia and neoplasia for men at this age (Starling. J.J. et al, *Monoclonal Antibodies and Cancer* pp. 253-286 (1984), New York, Marcel Dekker), specifically incorporated herein by reference, it is possible that this specimen was contaminated with cells that were not normal. This apparent low reactivity to normal prostate by TURP-27 was also examined by quantitative adsorption analysis (FIG. 1A). This technique suggested that the TURP-27 antigen was in normal prostate tissue but at a much lower concentration than in BPH and prostate adenocarcinoma (Table 2 and FIG. 1A). Of the normal prostate specimens examined in the immunoperoxidase assay (Table 3), only 10% of the ductal epithelial cells were reactive with the TURP-27 monoclonal antibody. This result was consistent with the low binding activity of TURP-27 in the solid-phase RIA and quantitative adsorption assay for these specimens. Collectively, the data demonstrates that the TURP-27 antigen should be a useful marker for benign and/or malignant growth.

(J) TURP-27 and TURP-73 vs Known Prostate Antibodies

Comparison of TURP-27 and TURP-73 with other monoclonal antibodies derived against prostate antigens demonstrates that TURP-27 and TURP-73 have defined new prostate organ- and tumor-associated antigens. The serological activity of monoclonal antibodies D83.21 (Starling, J.J. et al, *Cancer Res.*, 42:3084-3089 (1982) and Starling. J.J. et al, *Monoclonal Antibodies and Cancer*, pp. 253-286 (1984), New York, Marcel Dekker), both of which are specifically incorporated herein by reference, and P6.2 (Wright G.L. et al, *Cancer Res.*, 43:5509-5516 (1983) and Starling, J.J. et al, *Monoclonal Antibodies and Cancer*, pp. 253-286 (1984). New York, Marcel Dekker)), both of which are specifically incorporated herein by reference, derived against the DU145 cell line, described by Mickey, D.D. et al, *Prog. Clin. Biol. Res.*, 37:67-84 (1980), specifically incorporated herein by reference and the PC-3 cell line, described by Kaighn, M.E. et al, *Prog. Clin. Biol. Res.*, 37:85-109 (1980), respectively, both of which are specifically incorporated herein by reference, is quite distinct from TURP-27 or TURP-73 in that TURP-27 does not bind to any cell line tested (Table 1) and TURP-73 binds strongly to BPH specimens (Tables 2 and 3); while neither D83.21 or P6.2 have a high affinity for BPH. Furthermore, in a limited study neither D83.21 nor P6.2 blocked the binding of TURP-27 and TURP-73 to their respective targets.

Monoclonal antibody Pro-3 described by Ware, J.L. et al, *Cancer Res.*, 42:1215-1222 (1982), specifically incorporated herein by reference, produced against the PC-3 cell line, binds strongly to the immunizing cell line but not to DU145 prostate tumor cells and reacts much more strongly with prostate adenocarcinoma than with BPH tissues. TURP-27, on the other hand, does not bind to either the DU145 or the PC-3 cell line while TURP-73 binds to both cell lines (Table 1). TURP-27 and TURP-73 also react strongly with both BPH and malignant prostate tissue (Tables 2 and 3 and FIGS. 2A and 2B).

Monoclonal antibodies 35 and 24 have been described by Frankel, A.E. et al, *Proc. Natl. Acad. Sci. USA*, 99:903-907 (1982), specifically incorporated herein by reference. These monoclonal antibodies are different from TURP-27 and TURP-73 in that monoclonal antibody 24 reacts with the PC-3 cell line and also binds more strongly to normal prostate than to malignant prostate tissue, Frankel, A.E. et al, *Proc. Natl. Acad. Sci. USA*, 99:903-907 (1982), specifically incorporated herein by reference. On the other hand, TURP-27 does not bind to PC-3 cells (Table 1) and this monoclonal antibody reacts more strongly with prostate adenocarcinoma than to normal prostate (Tables 2 and 4 and FIG. 2A). Monoclonal antibody 35 is distinct from TURP-73 in that monoclonal antibody 35 binds to T-24 bladder carcinoma cells and to normal breast tissue, Frankel, A.E. et al, *Proc. Natl. Acad. Sci. USA*, 99:903-907 (1982), specifically incorporated herein by reference while TURP-73 reacts with neither of these antigen sources (Tables 1, 2, and 3).

A monoclonal antibody, KR-P8, directed against the PC-3 prostate tumor cell line has been described by Raynor, R.H. et al, *J. Natl. Cancer Inst.*, 73:617-625 (1984), specifically incorporated herein by reference. The KR-P8 antigen was stated to be a new prostate-specific marker even though extensive binding studies of the monoclonal antibody to a large panel of human normal and tumor tissues was not performed. TURP-27 does not appear to be directed against the KR-P8 antigen because TURP-27 does not react with PC-3 cells (Table 1). TURP-73 can also be distinguished from KR-P8 in that the immunoperoxidase staining of the TURP-73 antigen is localized at the luminal border of columnar epithelial cells, while the KR-P8 antigen is found extensively in the cytoplasm of these cells (Raynor, R.H. et al, *J. Natl. Cancer Inst.*, 73:617-625 (1984)), specifically incorporated herein by reference.

Three monoclonal antibodies produced to the PC-3 immunogen have been described by Carroll, A.M. et al, *Clin. Immunol. Immunopath.*, 33:268-281 (1984). specifically incorporated herein by reference. All three monoclonals bind to the PC-3 targets whereas TURP-27 does not bind to any tumor cell line tested (Table 1). TURP-73 can also be distinguished from these three monoclonal antibodies by the lack of the binding of TURP-73 to the breast adenocarcinoma cell line BT-20 (Table 1) and breast carcinoma tissue (Table 3): both of which were strongly bound by one of these monoclonal antibodies. These monoclonal antibodies were also found to stain sections of normal breast tissue; whereas. TURP-73 failed to bind normal breast tissues (Tables 2 and 3).

A panel of eight monoclonal antibodies directed against human prostate cancer cell lines was recently described by Lindgren, J. et al, *Hybridoma*, 4:37-45 (1985), specially incorporated herein by reference. Seven of these monoclonal antibodies did not react strongly with fixed tissues in the immunoperoxidase assay which distinguishes them from TURP-27 and TURP-73. The one immunohistochemically reactive monoclonal antibody described in this report bound to a nuclear antigen present in all cells tested which is clearly different from the pattern seen by TURP-27 and TURP-73 (Table 3).

A human IgM monoclonal antibody designated MGH-7, produced by fusing lymphocytes from a regional draining lymph node from a patient with prostate carcinoma with murine myeloma cells, was recently described by Lowe, D.H. et al, *J. Urol.*, 132:780-785 (1984), specifically incorporated herein by reference. This antibody bound both normal and malignant prostate tissues and in this way is similar to the binding of both TURP-27 and TURP-73. What distinguishes TURP-27 from MGH-7 is that TURP-27 does not bind to any human cell lines; whereas, MGH-7 binds to both the LNCaP and PC-3 prostate tumor cell lines but not to the DU145 prostate tumor cell line. The lack of binding to DU145 cells and the binding to lung adenocarcinoma cells distinguishes the binding of MGH-7 from TURP-73, which does not react to either of these cells types (Tables 1 and 3).

EXAMPLE 2

Radioimmunolocalization

TURP-73 was analyzed for its ability to target human tumors growing in nude mice. More specifically, intact affinity purified TURP-73 was labelled with 1.0 mCi Na $I^{125}$ by the Iodobead method described above to a specific activity of approximately 4.0 $\mu Ci/\mu g$. The antigenic specificity was determined by a direct binding solid phase RIA as described above, and biodistribution studies were performed as follows. Groups of six LS174T (colon carcinoma) or PC-3 (prostate carcinoma) tumor-bearing mice were injected i.v. with 8.0 $\mu Ci$ of either $I^{125}$ TURP-73 or $I^{125}$ CM72 (an isotype matched unrelated monoclonal antibody). Groups of mice were sacrificed 24, 48, 72 and 96 hours and the organs were removed weighed and counted in a gamma counter to determine the biodistribution of the $I^{125}$ TURP-73 or $I^{125}$ CM72. The results of the biodistribution data for TURP-73 localization of PC-3 prostate tumor xenografts are shown in Table 6 below.

TABLE 6

Biodistribution for TURP-73 Localization of PC-3 Prostate Tumor Xenografts

| TISSUE | TURP-73 | | CM72 | |
|---|---|---|---|---|
| | % ID/g$^a$ | T/T$^b$ | % ID/g | T/T |
| Tumor | 11.40 ± 0.34 | 1.00 ± 0.00 | 1.41 ± 0.22 | 1.00 ± 0.00 |
| Blood | 3.96 ± 0.40 | 3.60 ± 0.05 | 2.53 ± 0.21 | 0.53 ± 0.09 |
| Liver | 1.80 ± 0.73 | 6.80 ± 0.18 | 0.91 ± 0.09 | 1.83 ± 0.16 |
| Lung | 2.20 ± 0.49 | 5.20 ± 0.16 | 1.00 ± 0.04 | 1.62 ± 0.20 |
| Spleen | 1.92 ± 0.44 | 8.30 ± 0.25 | 0.82 ± 0.10 | 2.01 ± 0.12 |
| Kidney | 2.02 ± 0.86 | 7.94 ± 0.07 | 0.86 ± 0.07 | 1.53 ± 0.18 |

$^a$percent of the injected dose of labelled antibody remaining per gram of tissues. Mean ± S.D.
$^b$tumor to tissue ratio. Mean ± S.D.

As the results in Table 6 above demonstrate. TURP-73 targeted the PC-3 tumor, concentrating a mean of 11.30% of the injected dose of $I^{125}$ TURP-73, compared with a mean of only 1.41% of the injected dose of the IgG$_{2a}$ isotype matched control antibody, $I^{125}$ CM72. High tumor to tissue ratios of labelled TURP-73 in the liver, spleen, kidney and lung demonstrate that TURP-73 should be applicable for radioimaging prostate as well as colon tumors.

It will be apparent to those skilled in the art that various modifications and variations can be made to the processes and products of the present invention. Thus, it is intended that the present invention covers these modifications and variations of this invention provided they come within the scope of the appended claims and their equivalents.

What is claimed is:

1. A monoclonal antibody having binding specificity to human prostate tumor-associated membrane antigens that;
    (a) does not having binding specificity to prostate-specific antigen, prostatic acid phosphatase, normal lung, lung carcinoma, bladder carcinoma, normal breast, normal liver, breast carcinoma or normal spleen; and
    (b) does not have binding specificity to both DU145 and PCP-3.

2. The monoclonal antibody as claimed in claim 1, wherein said monoclonal, antibody is TURP-27 having the identifying characteristics of the antibody secreted by hybridoma ATCC No. HB 8977.

3. A method for diagnosing prostate tumors and metastases thereof comprising:
    (a) obtaining a sample of body fluid from a patient;
    (b) exposing the body fluid to a monoclonal antibody as claimed in claim 1 wherein said antibody is secreted by hybridoma TURP-27 with ATCC No. HB 8977;
    (c) determining the amount of monoclonal antibody binding to substances present in the body fluid; and
    (d) comparing the amount of monoclonal antibody bound to body fluid substances to a predetermined base level to ascertain the presence of prostate tumors or metastases thereof.

4. The method as claimed in claim 3, wherein said body fluid is one member selected from the group consisting of blood, serum, seminal plasma, semen, urine and prostatic fluid.

5. The method as claimed in claim 3, wherein the amount of monoclonal antibody binding to substances present in the body fluid is determined by means of a radioimmunoassay.

6. The method as claimed in claim 3, wherein the amount of monoclonal antibody binding to substances present in the body fluid is determined by means of an enzyme immunoassay.

7. A method for diagnosing the presence of prostate tumors or metastases thereof comprising:
    (a) administering to a patient, a monoclonal antibody as claimed in claim 1 wherein said antibody is secreted hybridoma TURP-27 with ATCC No. HB 8977 wherein said monoclonal antibody is conjugated to a marker; and
    (b) exposing the patient to a detection device to identify areas of marker corresponding to prostate tumor sites or metastatic sites thereof.

8. The method as claimed in claim 7, wherein the marker is a nuclear magnetic spin-resonance isotope and wherein the detection device is a nuclear magnetic imaging device.

9. The method as claimed in claim 8, wherein marker is gadolinium.

10. The method as claimed in claim 7, wherein the marker is a radioactive substance and wherein the detection device is a gamma scintillation camera.

11. The method as claimed in claim 10, wherein the radioactive substance is one member selected from the group consisting of $I^{125}$, $I^{131}$, $I^{123}$, $In^{111}$,m $In^{113}$, $Ga^{67}$, $Ga^{68}$, $Ru^{97}$, $R^{103}$, $Hg^{197}$, $Hg^{203}$ and $Tc^{99m}$.

12. The method as claimed in claim 11, wherein the radioactive substance is $In^{111}$ or $Tc^{99M}$.

* * * * *